US008101733B1

(12) United States Patent
Shriver et al.

(10) Patent No.: US 8,101,733 B1
(45) Date of Patent: Jan. 24, 2012

(54) METHODS OF EVALUATING MIXTURES OF POLYSACCHARIDES

(75) Inventors: Zachary Shriver, Cambridge, MA (US);
Cuihua Liu, Belmont, MA (US); Nur Sibel Gunay, Brookline, MA (US);
Ishan Capila, Ashland, MA (US);
Ganesh Venkataraman, Bedford, MA (US)

(73) Assignee: Momenta Pharmaceuticals, Inc., Cambridge, MA (US)

(*) Notice: Subject to any disclaimer, the term of this patent is extended or adjusted under 35 U.S.C. 154(b) by 905 days.

(21) Appl. No.: 11/426,765

(22) Filed: Jun. 27, 2006

(51) Int. Cl.
*A61K 31/727* (2006.01)
*C08B 37/10* (2006.01)

(52) U.S. Cl. ............................. 536/21; 514/56

(58) Field of Classification Search ............... None
See application file for complete search history.

(56) References Cited

U.S. PATENT DOCUMENTS

| | | | |
|---|---|---|---|
| 4,692,435 | A | 9/1987 | Lormeau |
| 5,389,618 | A | 2/1995 | Debrie |
| 6,617,316 | B1 | 9/2003 | Mourier et al. |
| RE38,743 | E | 6/2005 | Debrie |
| 7,083,937 | B2 | 8/2006 | Sasisekharan et al. |
| 7,575,886 | B2 * | 8/2009 | Venkataraman et al. ....... 435/18 |
| 2003/0203385 | A1 | 10/2003 | Venkataraman et al. |
| 2004/0265943 | A1 | 12/2004 | Viskov et al. |
| 2005/0119477 | A1 | 6/2005 | Mourier et al. |
| 2005/0186679 | A1 | 8/2005 | Viskov et al. |
| 2005/0215519 | A1 | 9/2005 | Viskov et al. |
| 2005/0288252 | A1 * | 12/2005 | Nurcombe et al. .............. 514/56 |
| 2006/0024664 | A1 | 2/2006 | Sasisekharan et al. |
| 2007/0098708 | A1 * | 5/2007 | Myette ........................ 424/94.61 |
| 2007/0161073 | A1 | 7/2007 | Sasisekharan et al. |

FOREIGN PATENT DOCUMENTS

| | | |
|---|---|---|
| EP | 1586588 | 10/2000 |
| EP | 1580197 | 9/2005 |
| EP | 1582531 | 10/2005 |
| WO | WO 01/29055 | 4/2001 |
| WO | WO 03/078960 | 9/2003 |
| WO | WO 2004/027087 | 4/2004 |
| WO | WO 2005/009040 | 1/2005 |
| WO | WO 2005/080438 | 9/2005 |
| WO | WO 2005/090411 | 9/2005 |

OTHER PUBLICATIONS

Desai et al., "Molecular weight of low molecular weight heparins by 13C nuclear magnetic resonance spectroscopy," Carbohydrate Research, 255, (1994) pp. 193-212.
Malsch et al., "High-resolution capillary electrophoresis and polyacrylamide gel electophoresis of heparins," Journal of Chromatography A. 716. (1995) pp. 258-268.
Sundaram et al., "Rational design of low-molecular weight heparins with improved in vivo activity," PNAS, 100(2), Jan. 21, 2003, pp. 651-656.
Ampofo, S. et al., "Disaccharide Compositional Analysis of Heparin and Heparan Sulfate Using Capillary Zone Electrophoresis," *Analytical Biochem.*, 199:249-255 (1991).
Da Col, R. et al., "Characterization of the Chemical Structure of Sulphated Glycosaminoglycans After Enzymatic Digestion. Application for Liquid Chromatography—Mass Spectrometry with an Atmospheric Pressure Interface," *J. of Chromatography*, 647:289-300 (1993).
Desai, U. et al., "Oligosaccharide Composition of Heparin and Low-molecular-weight Heparins by Capillary Electrophoresis," *Analytical Biochem.*, 213:120-127 (1993).
Ernst, S. et al., "Direct Evidence for Predominantly Exolytic Processive Mechanism for Depolymerization of Heparin-like Glycosaminoglycans by Heparinase I," *PNAS*, 95:4182-4187 (1998).
Guo, Y. et al., "The Disaccharide of Heparins and Heparan Sulfates," *Analytical Biochem.*, 176:96-104 (1989).
Imanari, T. et al., "High-performance Liquid Chromatographic Analysis of Glycosaminoglycan-derived Oligosaccharides," *J. of Chromatography A*, 720:275-293 (1996).
Karamanos, N. et al., "Ion-pair High-performance Liquid Chromatography for Determining Disaccharide Composition in Heparin and Heparan Sulphate," *J. of Chromatography A*, 765:169-179 (1997).
Kariya, Y. et al., "Disaccharide Analysis of Heparin and Heparan Sulfate Using Deaminative Cleavage with Nitrous Acid and Subsequent Labeling with Paranitrophenyl Hydrazine," *J. Biochem.* (Tokyo), 123(2):240-6 (1998) Abstract Only.
Kinoshita, A. et al., "Microanalysis of Glycosaminoglycan-derived Oligosaccharides Labeled with a Fluorophore 2-aminobenzamide by High-performance Liquid Chromatography: Application to Disaccharide Composition Analysis of Exosequencing of Oligosaccharides," *Analytical Biochem.*, 269:367-378 (1999).
Lamari, F. et al., "Analysis of Glycosaminoglycan-derived Disaccharides in Biologic Samples by Capillary Electrophoresis and Protocol for Sequencing Glycosaminoglycans," *Biomedical Chromatography*, 16:95-102 (2002).
Lee, G. et al., "Separation of Reduced Disaccharides Derived from Glycosaminoglycans by High-performance Liquid Chromatography," *J. Of Chromatography*, 212:65-73 (1981).
Lindhart, R. et al., "Mapping and Quantification of the Major Oligosaccharide Components of Heparin," *Biochem. Journal*, 254:781-787 (1988).
Linhardt, R. et al., "Oligosaccharide Mapping of Low Molecular Weight Heparins: Structure and Activity Differences," *J. of Medicinal Chem.*, 33(6):1639-1645 (1990).
Lindhardt, R. et al., "New Methodologies in Heparin Structure Analysis and the Generation of LMW Heparins," *Heparin and Related Polysaccharides*, 37-47, ed. D.A. Lane et al., Plenum Press, New York (1992).
Merchant, K. et al., "Structure of Heparin-derived Tetrasaccharides," Biochem. Journal, 229:369-377 (1985).
Militsopoulou, M. et al., "Determination of 12 Heparin- and Heparan Sulfate-derived Disaccharides as 2-aminoacridone Derivatives by Capillary Zone Electrophoresis Using Ultraviolet and Laser-induced Flourescence Detection," *Electrophoresis*, 23:1104-1109 (2002).
Park, Y. et al., "Purification and Characterization of Heparin Sulphate Proteoglycan from Bovine Brain," Biochem. Journal, 344:723-730 (1999).

(Continued)

*Primary Examiner* — Eric S Olson
(74) *Attorney, Agent, or Firm* — Lando & Anastasi, LLP

(57) ABSTRACT

Methods for analyzing mixtures of polysaccharides, for example heparin or a LMWH, using reduce end labeling are described. In general, the mixture of polysaccharides includes polysaccharides having a desired structural moiety. In some instances, one or more polysaccharides in the mixture are chemically modified prior to analysis.

21 Claims, 9 Drawing Sheets

OTHER PUBLICATIONS

Pervin, A. et al., "Separation of Glycosaminoglycan-derived Oligosaccharides by Capillary Electrophoresis Using Reverse Polarity," *Analytical Biochem.*, 221:182-188 (1994).

Rhomberg, A. et al., "Mass Spectrometric and Capillary Electrophoretic Investigation of the Enzymatic Degradation of Heparin-like Glycosaminoglycans," PNAS, 95:4167-4181 (1998).

Rice, K. et al., "High-performance Liquid Chromatographic Separation of Heparin-derived Oligosaccharides," *Analytical Biochem.*, 150(2):325-31 (1985) Abstract Only.

Ruiz-:Calero, V. et al., "Pressure-assisted Capillary Electrophoresis-electrospray Ion Trap Mass Spectrometry for the Analysis of Heparin Depolymerised Disaccharides," *J. of Chromatography A*, 914:277-291 (2001).

Ruiz-Calero, V. et al., "Use of Reversed Polarity and a Pressure Gradient in the Analysis of Disaccharide Composition of Heparin by Capillary Electrophoresis," *J. of Chromatography A*, 828:497-508 (1998).

Saad, O. et al., "Compositional Analysis and Quantification of Heparin and Heparan Sulfate by Electrospray Ionization Ion Trap Mass Spectrometry," *Anal. Chem.*, 75:2985-2995 (2003).

Scapol, L. et al., "Capillary Electrophoresis of Heparin and Dermatan Sulfate Unsaturated Disaccharides with Triethvlamine Acetonitrile as Elecrolyte Additives," *J. Of Chromatography A.*, 735:367-374, (1996) /ESO/.

Thanawiroon, C. et al., "Separation of a Complex Mixture of Heparin-derived Oligosaccharides Using Reversed-phase High-performance Liquid Chromatography," *J. of Chromatography A*, 1014:215-223 (2003).

Thanawiroon, C. et al., "Liquid Chromatography/Mass Spectrometry Sequencing Approach for Highly Sulfated Heparin-derived Oligosaccharides," *J. Of Biological Chem.*, 279(4):2608-2615 (2004).

Toida, T. et al., "Structural Differences and the Presence of Unsubstituted Amino Groups in Heparan Sulphates from Different Tissues and Species," *Biochem. Journal*, 322:499-506 (1997).

Toyoda, H. et al., "Rapid and Sensitive Analysis of Disaccharide Composition in Heparin and Heparan Sulfate by Reversed-phase Ion-pair Chromatography on a 2 μm Porous Silica Gel Column," *J. of Chromatogrphy A*, 830:197-201 (1999).

Volpi, N., "Characterization of Heparins with Different Relative Molecular Masses (from 11 600 to 1600) by Various Analytical Techniques," *J. of Chromatography*, 622:13-20 (1993).

Volpi, N., "Hyaluronic Acid and Chondroitin Sulfate Unsaturated Disaccharides Analysis by High-Performance Liquid Chromatography and Fluorimetric Detection with Dansylhydrazine," *Analytical Biochem.*, 277:19-24 (2000).

Vynios, D. et al., "Advances in Analysis of Glycosaminoglycans: Its Applications for the Assessment of Physiological and Pathological States of Connective Tissues," *J. Of Chromatography B*, 781:21-38 (2002).

Yoshida, K., "Analysis of Unsaturated Disaccharides form Glycosaminoglycuronan by High-performance Liquid Chromatography;" *Analytical Biochem.*, 117:327-332 (1989).

\* cited by examiner wherein, X = H, SO$_3^-$, Y = Ac, SO$_3^-$ (Ac is C(O)CH$_3$), and n = 0 – 17.

METHODS OF EVALUATING MIXTURES OF POLYSACCHARIDES

The invention relate to methods of analyzing samples containing complex carbohydrates, e.g., low molecular weight heparins (LMWHs), most preferably enoxaparin, for chains having a particular structure, e.g., a 1,6 anhydro structure, using end labeling, e.g., of a reducing end structure.

BACKGROUND

Complex polysaccharides have been used as pharmaceutical interventions in a number of disease processes, including oncology, inflammatory diseases, and thrombosis. Examples of pharmaceutical interventions in this class are hyaluronic acid, an aid to wound healing and anti-cancer agent, and heparin, a potent anticoagulant and anti-thrombotic agent. Complex polysaccharides elicit their function primarily through binding soluble protein signaling molecules, including growth factors, cytokines and morphogens present at the cell surface and within the extracellular matrices between cells, as well as their cognate receptors present within this environment. In so doing, these complex polysaccharides effect critical changes in extracellular and intracellular signaling pathways important to cell and tissue function. For example, heparin binds to the coagulation inhibitor antithrombin III promoting its ability to inhibit factors IIa and Xa. Being able to identify and quantify the type and extent of chemical modification of a polysaccharide chain as a result of isolation and processing would be of benefit both from (1) a process control standpoint and (2) understanding biologically specific structure-function relationships.

SUMMARY

Complex polysaccharide drug products can be isolated or derived from natural sources and are complex mixtures of polysaccharide chains that differ from one another both in terms of size and chemical sequence that comprises each polysaccharide chain. Chain sequence differences can arise both from differences intrinsic to the cell and tissue-specific biosynthesis pathway by which these complex polysaccharides are made as well as from differences that arise from the process of isolating or preparing polysaccharide substances from natural sources. For example, the low molecular weight heparins (LMWHs) are derived from unfractionated heparin primarily through chemical or enzymatic depolymerization of the polysaccharide chains. Thus, different LMWHs scan be made by various depolymerization processes. A process used to make as LMWH can cause one or more unique structural modifications to the polysaccharide chains of the polysaccharide drug, such as heparin. For example, nitrous acid depolymerization of heparin results in the formation of a 2,5-anhydromannose at the reducing end, which can be reduced to form an alcohol. Conversely, depolymerization through esterification of the carboxylate functional group on the uronic acid followed by β-elimination results in the formation of a $\Delta^{4,5}$ double bond on the non-reducing end as well as the formation of a 1,6-anhydro derivatives on some chains. Other structural modifications that arise from depolymerization can include a change in the amount or number of chains in the sample that include a structural moiety, e.g., structure that occurs naturally in the material used to make the LMWH, as compared to, e.g., the starting material, e.g., unfractionated heparin. As a result of these and other structural changes, different LMWHs can have distinct pharmacological and/or structural profiles.

Accordingly, methods for measuring the presence and extent of selected structures which, e.g., arise from modifications that occur (e.g., during preparation) to complex polysaccharide drug substances, are beneficial to characterize the polysaccharide mixtures. This is true either from a process standpoint, to monitor or ensure batch-to-batch consistency and quality, (e.g., to monitor or evaluate similarity with a reference structure), or from a structure-activity prospective, to evaluate or ensure biological equivalence. This is especially important since some of the modified structures present may possess or impinge on the biological activity. Novel methods for analyzing modified structures present in complex polysaccharides are described herein.

In one aspect, the invention provides methods of evaluating a polysaccharide mixture, e.g., a heterogeneous population of sulfated polysaccharides, by evaluating one or more parameters related to a species or species described herein, e.g., a 1,6 anhydro derivative or derivatives. Such parameters can include the presence, relative distribution, or quantity of a species or species described herein, e.g., 1,6 anhydro derivative disclosed herein. The method is particularly useful for analyzing preparations of LMWHs, e.g., enoxaparin preparations or preparations having similar properties. As is discussed in more detail below, methods disclosed herein can be used to monitor or guide the production of LMWHs, e.g., enoxaparin. The methods described herein can be used rapidly and efficiently and many do not include or require isolation of the species being analyzed.

In one embodiment, the polysaccharide mixture is digested, e.g., chemically and/or enzymatically digested, e.g., incompletely or preferably, completely digested. The enzymatic digestion can be carried out with one or more heparin degrading enzymes, e.g., one or more heparin degrading enzymes described herein.

In one embodiment, the polysaccharide mixture is size fractionated, e.g., by a method described herein. One or more fraction of the polysaccharide mixture, e.g., one or more of a tetrasaccharide, hexasaccharide, octasaccharide, decasaccharide, dodecasaccharide and tetradecasaccharide fraction, can be analyzed or evaluated by the methods described herein. The polysaccharide mixture can be size fractionated, e.g., by FPLC, GPC-MS, size-exclusion chromatography, ion exchange HPLC, or ion-pairing reverse phase HPLC.

The methods described herein can be used to analyze complex mixtures of polysaccharides from a variety of sources. Methods can be used to analyze a sample from a human or veterinary subject, an experimental animal, a cell, or any commercially available preparation of polysaccharides, e.g., unfractionated heparin (UFH) or LMWH, including but not limited to enoxaparin (Lovenox™ or Clexane™); dalteparin (Fragmin™); certoparin (Sandoparin™); ardeparin (Normiflo™); nadroparin (Fraxiparin™); parnaparin (Fluxum™); reviparin (Clivarin™); tinzaparin (Innohep™ or Logiparin™), fondaparinux (Arixtra™). Particularly useful embodiments are used to monitor one or more structural or functional properties in the production or testing of a drug, e.g., enoxaparin or a similar substance.

In one aspect, the invention features a method of analyzing or processing a polysaccharide mixture, e.g., a LMWH preparation, e.g., an enoxaparin preparation, that includes: providing a polysaccharide mixture comprising a plurality of polysaccharides; reacting a reducing end of at least a portion of the polysaccharides in the polysaccharide mixture with a reactive moiety; and quantifying a polysaccharide in the polysaccharide mixture, thereby analyzing or processing the mixture.

In one embodiment, the polysaccharide mixture includes one or more polysaccharides having a closed confirmation at the reducing end, e.g., a 1,6 anhydro structural moiety or 2,5 anhydro structural moiety, and e.g., one or more polysaccharides having an open confirmation at the reducing end, e.g., an aldehyde. In one embodiment, either the closed confirmation structural moiety, e.g., a 1,6 anhydro structural moiety or a 2,5 anhydro structural moiety, or the open confirmation structural moiety in the mixture is specifically reacted with a reactive moiety. In one embodiment, either the open confirmation structural moiety or the closed confirmation structural moiety is quantified, e.g., by determining the amount of reacted saccharide.

In one embodiment, substantially all or all of the polysaccharides in the mixture include an open confirmation at the reducing end. Preferably, the polysaccharides in the mixture being quantified can be distinguished front other polysaccharides in the mixture based upon a structural moiety at the non-reducing end, e.g., an iduronic acid, a glucuronic acid or a Δ4,5 double bond.

In one embodiment, the reactive moiety has one or more of the following properties: it does not react with a closed confirmation structural moiety, e.g., a 1,6 anhydro structural moiety and/or a 2,5 anhydro structural moiety; and it reacts with free amines of a polysaccharide.

In one embodiment, at least a portion of the open confirmation structural moieties are reacted with a biotin derivative, biotin hydrazide, at the reducing end of a saccharide moiety. The term "reducing end of a saccharide moiety" also refers to saccharides having "an open ring confirmation structural moiety" at the reducing end.

In another embodiment, the reactive moiety comprises a peptide that includes an aminooxyacetyl moiety at the N-terminus. In one embodiment, the peptide further comprises a biotin moiety.

In one embodiment, the polysaccharide mixture is enoxaparin and the method includes determining the size distribution of the 1,6 anhydro structural moiety. In one embodiment, the amount of the 1,6 anhydro structural moiety is determined using e.g., a substrate that preferentially binds a reducing end saccharide moiety of the sample over the 1,6 anhydro structural moiety. In one embodiment, the reduce end saccharide moieties are labeled, directly or indirectly, with biotin and the substrate preferentially binds biotin, e.g., the substrate is coated with streptavidin. In one embodiment, the amount of 1,6 anhydro structural moiety is determined by comparing the UV absorbance (e.g., UV absorbance at about 232 nm) of the sample prior to contacting the sample with a substrate that preferentially binds the reducing and saccharide moieties of the sample, and the UV absorbance (e.g., UV absorbance at about 232 nm) of the sample after contact with the substrate. In one embodiment, the determination is made using one or more of HPLC, CE and UV absorbance.

In one embodiment, the method includes detecting a structure associated with a non-reducing end of at least a portion of the polysaccharides in the polysaccharide mixture, e.g., by ultraviolet (UV) absorption; reacting a reducing end of at least a portion of the polysaccharides in the polysaccharide mixture with a reactive moiety; and quantifying a polysaccharide in the polysaccharide mixture, thereby analyzing the polysaccharide mixture.

In one embodiment, the structure associated with the non-reducing end of at least a portion of the polysaccharides is a structure that can be detected by UV absorbance, e.g., a Δ4,5 double bond, e.g., a $\Delta U_{2S}$ and/or $\Delta U$. In one embodiment, the quantity of the structure associated with the non-reducing end is determined. In one embodiment, the polysaccharide mixture is an enoxaparin sample and the quantity of $\Delta U_{2S}$ is indicative of the total amount of chains in the sample. In another embodiment, the polysaccharide mixture is a LMWH sample and the quantity of $\Delta U$ is indicative of a portion of chains in the sample, e.g., a portion of the chains having a modified non-reducing end structure, e.g., a Δ4,5 double bond, e.g., as compared to a iduronic acid and/or glucuronic acid at the non-reducing end.

In one embodiment, the reducing end of a saccharide moiety in a LMWH sample is specifically reacted with the reactive moiety e.g., a detectable reactive moiety. In one embodiment, the reducing end of the saccharide moiety is quantified, e.g., by determining the amount of reacted saccharide. In one embodiment, the reacted saccharide is indicative of the total amount of chains in the sample. In one embodiment, at least a portion (e.g., but not all) of the saccharide moieties are reacted with a label, e.g., a fluorescent label at the reducing end of the saccharide moiety.

In one embodiment, the polysaccharide mixture is a LMWH preparation and the method includes determining the amount or the size distribution of a Δ4,5 double bond non-reducing end structural moiety, e.g., a ΔU non-reducing end structural moiety. In one embodiment, the amount of the Δ4,5 double bond non-reducing end structural moiety, e.g., a ΔU non-reducing end structural moiety, is determined based upon the total of reducing end labeled chains in the sample, e.g., the total of reduce end labeled saccharide moieties is indicative of the total amount of chains in the sample. In one embodiment, the amount of Δ4,5 double bond non-reducing end structural moiety, e.g., a ΔU non-reducing end structural moiety, is determined by comparing the total reducing end labeled portion of the sample, e.g., the total of fluorescently labeled reduce end portion of the sample, to UV absorbance.

In one embodiment, the polysaccharide mixture is an enoxaparin preparation and the method includes determining the amount or the size distribution of the 1,6 anhydro structural moiety. In one embodiment, the amount of the 1,6 anhydro structural moiety is determined based upon the total of reducing end labeled chains in the sample. In one embodiment, the amount of 1,6 anhydro structural moiety is determined by comparing the UV absorbance to the total reducing end labeled portion of the simple, e.g., the total of fluorescently labeled reduce end portion of the sample. In one embodiment, the method includes determining the amount or the size distribution of the 1,6 anhydro structural moiety. In one embodiment, the amount of the 1,6 anhydro structural moiety is determined using, e.g., a fluorescent reactive moiety. In one embodiment, the amount of 1,6 anhydro structural moiety is determined by comparing the UV absorbance (e.g., UV absorbance at about 232 nm) of the sample to the fluorescence of the sample. In one embodiment, the determination is made using one or more of HPLC, CE and UV absorbance. In one embodiment, the sample is digested, e.g., the method can further include digesting, e.g., chemically and/or enzymatically digesting, the sample. In one embodiment, the sample is completely digested. The enzymatic digestion can be carried out with one or more heparin degrading enzymes, e.g., one or more heparin degrading enzymes described herein.

In one embodiment, the digested mixture comprises one or more monosaccharide, disaccharide, and/or tetrasaccharide.

In one embodiment, the 1,6 anhydro structural moiety includes one or more compounds selected from the group consisting of:

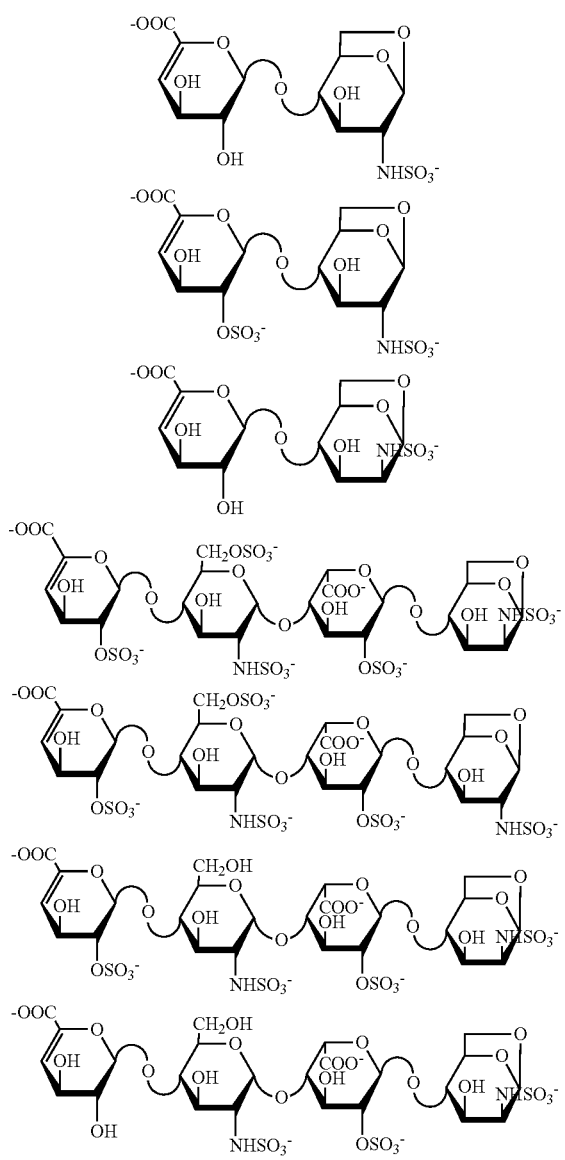

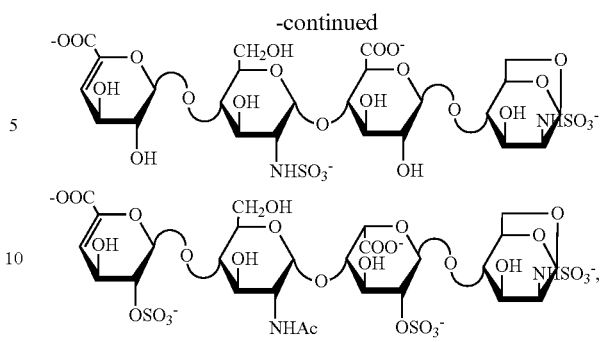

or mixtures thereof.

In one embodiment, the enoxaparin sample is size fractionated, e.g., the method can include fractionating the sample, and e.g., the size fractionated sample includes one or more of tetrasaccharides, hexasaccharides, octasaccharides, decasaccharides, or dodecasaccharides. The method can further include analyzing one or more fractions of the sample to determine the presence of a saccharide moiety specie or species without isolating the specie or species from the sample. For example, in one embodiment, the method can further include analyzing one or more fractions of the sample to determine the presence of a 1,6 anhydro structural moiety without isolating the species which include the 1,6 anhydro moiety. In one embodiment, the tetrasaccharide, hexasaccharide, octasaccharide, decasaccharide and/or dodecasaccharide is present in the sample and the sample is not digested to produce the tetrasaccharide, hexasaccharide, octasaccharide, decasaccharide and/or dodecasaccharide. In one embodiment, the sample is size fractionated using FLPC, GPS-MS, size-exclusion chromatography, ion exchange HPLC, or ion-pairing reverse phase HPLC. In one embodiment, a size defined saccharide fraction (e.g., a tetrasaccharide, hexasaccharide, octasaccharide, decasaccharide, and/or dodecasaccharide fraction) can be analyzed for a 1,6 anhydro structural moiety at the reducing end, as an indicator of total 1,6 anhydro content in the unfractionated enoxaparin sample. In a preferred embodiment one or more size fractions is selected and is analyzed e.g., by a method described herein, for a moiety described herein, e.g., a 1,6 anhydro structural moiety.

In one embodiment, the 1,6 anhydro structural moiety includes one or more of:

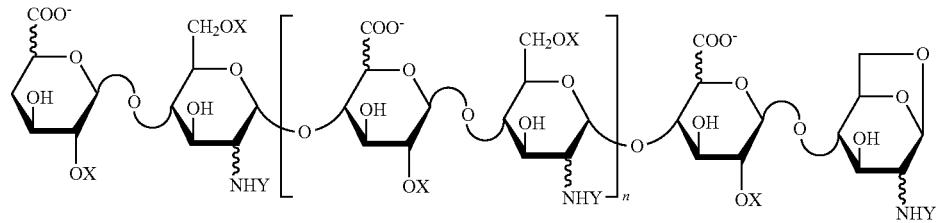

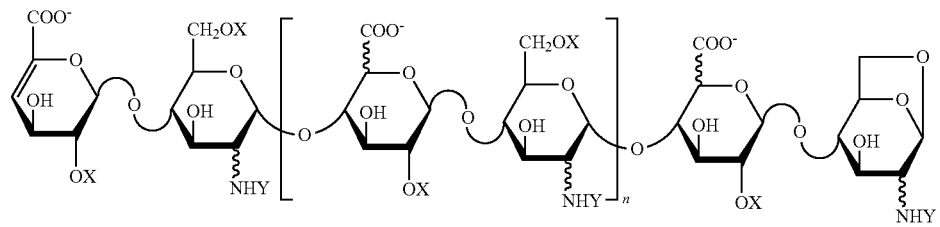

and mixtures thereof, wherein, X=H, $SO_3^-$, Y=Ac, $SO_3^-$ (Ac is $C(O)CH_3$), and n=0–17.

In one embodiment, the total percentage of the 1,6 anhydro structural moiety, e.g., the total percentage of chains having 1,6 anhydro structural moieties, in the preparation ranges from 15 to 25% or 15 to 30%, e.g., by weight average molecular weight or mole %, and preferably the method includes determining or confirming that the moiety is in said range. In another embodiment, the total percentage of the 1,6 anhydro structural moiety, e.g., the total percentage of chains having 1,6 anhydro structural moieties, in the preparation ranges from 20 to 28%, e.g., by weight average molecular weight or mole %. In another embodiment, the total percentage of the 1,6 anhydro structural moiety, e.g., the total percentage of chains having a 1,6 anhydro structural moieties, in the preparation is compared to a reference standard, e.g., a label or spherical specification of a commercially available LMWH, e.g., a total percentage of 1,6 anhydro structural moieties, e.g., the total percentage of chains having 1,6 anhydro structural moieties, in the ranges from 15 to 25% or 15 to 30% (e.g., 20 to 28%), e.g., by weight average molecular weight or mole %.

In one embodiment, the method further includes making a decision, e.g., classified, selected, accented or discarded, released or withheld, process into drug product, shipped, formulated, labeled, packaged, released into commerce, sold, based, e.g., on the result of the determination or upon comparison to a reference standard.

In one aspect, the invention features a method of evaluating or processing a LMWH preparation, e.g., an enoxaparin preparation, that includes making a determination about a LMWH preparation, e.g., an enoxaparin preparation, based upon a method or analysis described herein. In one embodiment, the method further includes classifying, selecting, accepting or discarding, releasing or withholding, processing into a drug product, shipping, formulating, labeling, packaging, releasing into commerce, selling the preparation based, e.g., on the analysis. Thus, in a preferred embodiment, the party making the evaluation does not practice the method or analysis described herein but merely relies on results which are obtained by a method or analysis described herein.

In one aspect, the invention features a method of analyzing a process, e.g., manufacturing process, or a LMWH, an enoxaparin, e.g., an enoxaparin made by a selected process. The method includes: providing a LMWH sample, e.g., an enoxaparin sample; analyzing the sample using a reduce end labeling method, e.g., a method described herein, e.g., to identify and/or quantify a structure disclosed herein, e.g., a 1,6 anhydro structural moiety of the enoxaparin sample, thereby allowing analysis, e.g., quantitative analysis, of said structure, e.g., 1,6 anhydro structural moiety, in the sample. In other embodiments, a reduce end labeling method, e.g., a method described herein can be used to identify and/or quantify a Δ4,5 double bond structure, e.g., a ΔU and/or $\Delta U_{2S}$ structural moiety. In one embodiment, the method further includes comparing the amount, or size distribution of said structural moiety with a reference value, to thereby analyze the process.

In one embodiment, the structural moiety, e.g., the 1,6 structural moiety, is analyzed by a method which does not separate the structural moiety from a reducing structural moiety.

In one embodiment, the sample is size fractioned portion at the sample, e.g., method further includes size fractionating the sample, e.g., the enoxaparin sample. The size fractionated sample can include one or more tetrasaccharides, hexasaccharides, octasacchandes, decasaccharides, dodecasaccharides, or tetradeca-saccharides.

In one embodiment, the sample is digested, e.g., the method further includes digesting, e.g., chemically and/or enzymatically, the sample. In one embodiment, the sample is completely digested. Enzymatic digestion can be carried out with one or more heparin degrading enzymes, e.g., one or more heparin degrading enzymes described herein.

In one embodiment, the 1,6 anhydro structural moiety comprises a compound selected from the compounds of FIG. 1 and FIG. 2:

In one embodiment, the method includes determining the amount or the size distribution of the structural moiety, e.g., 1,6 anhydro structural moiety.

In one embodiment, the sample can include a total percentage of the structural moiety, e.g., the 1,6 anhydro structural moiety, e.g., the total percentage of chains having 1,6 anhydro structural moieties, in the preparation ranges from 15 to 25% or 15 to 30%, e.g., as measured by weight average molecular weight or mole %, and preferably the method includes determining or confirming that the moiety is in said range. In another embodiment, the sample can include a total percentage of the 1,6 anhydro structural moiety, e.g., the total percentage of chains having 1,6 anhydro structural moieties, in the preparation ranges from 20 to 28%, e.g., as measured by weight average molecular weight or mole %.

In one embodiment, the method includes determining if one or more of the structures of FIG. 1 and/or FIG. 2 is present.

In one embodiment, the sample, e.g., an undigested sample, e.g., a size fractionated sample of tetrasaccharides, hexasaceharides, octasaccharides, is analyzed to determine total percentage of tetrasaccharides, hexasaccharides or octasaccharides having a 1,6 anhydro structure at the reducing end.

In another embodiment, the amount or size distribution of a Δ4,5 double bond, e.g., a ΔU or $\Delta U_2 S$, at the non-reducing end is determined.

In one embodiment, the method further includes maintaining or altering the manufacturing process based, at least in part, upon the analysis.

In one aspect, the invention features a method of comparing two LMWH samples, e.g., enoxaparin samples, in a method of monitoring or controlling batch-to-batch variation or to compare a preparation to a reference standard. The method includes: providing a first sample, e.g., enoxaparin sample; providing the amount or size distribution of a structural moiety, e.g., a 1,6 structural moiety, in the first sample; optionally, providing a second sample, e.g., a second enoxaparin sample; providing the amount or size distribution of a structural moiety, e.g., a 1,6 structural moiety, in the second sample; and comparing the amount or size distribution the structural moiety, e.g., the 1,6 structural moiety, of the first sample with the structural moiety, e.g., the 1,6 structural moiety, of the second sample.

In one embodiment, the structural moiety is analyzed by a method described herein, e.g., is method which does not separate the 1,6 structural moiety from a reducing structural moiety.

In one embodiment, the method includes determining the amount or the size distribution of the 1,6 anhydro structural moiety.

In one embodiment, the sample can include a total percentage of the structural moiety, e.g., the 1,6 anhydro structural moiety, e.g., the total percentage of chains having 1,6 anhydro structural moieties, in the preparation ranges from 15 to 25% or 15 to 30%, e.g., by weight average molecular weight or mole %, and preferably the method includes determining or confirming that the moiety is in said range. In another embodiment, the sample can include a total percentage of the 1,6 anhydro structural moiety, e.g., the total percentage of chains having 1,6 anhydro structural moieties, in the preparation ranges from 20 to 28%, e.g., by weight average molecular weight or mole %.

In one embodiment, the method includes determining the amount or size distribution of a Δ4,5 double bond at the non-reducing end.

In one aspect, the invention features a method of analyzing a LMWH sample, e.g., an enoxaparin sample, that includes: providing a LMWH sample, e.g., an enoxaparin sample; determining the amount of a structural moiety, e.g., a 1,6 structural moiety, present in the sample without separating the structural moiety, e.g., the 1,6 structural moiety, from other chains in the sample that do not include the structural moiety, e.g., do not include a 1,6 structural moiety, thereby analyzing the sample. In one embodiment, the sample is analyzed by a method described herein.

In one aspect, the invention features a method of analyzing a heparin, that includes: depolymerizing a heparin by the action of nitrous acid to provide depolymerized heparin; proportioning the depolymerized heparin; and analyzing one or more fractions of the proportioned heparin to determine the presence of a first chemical moiety, thereby analyzing the heparin. In one embodiment, the heparin can be analyzed by a method described herein.

In one aspect, the invention features an enriched, isolated or purified population of polysaccharide chains having a 1,6 anhydro moiety at the reducing end.

The term "enriched population" as used herein is a preparation which is significantly enriched for chains having a specific reducing end structure. Enrichment can be with respect to a naturally occurring material, in UFH or in a LMWH, e.g., enoxaparin. In the case of a subject population which is present in UFH, the subject population is present in the enriched population at at least 2, 5, 10, 50 or 100 times the concentration (as determined, e.g., by weight/weight, chain number analysis or molarity) it is found in UFH. In the case of a subject population which is present in enoxaparin, the subject population is present in the enriched preparation at at least 2, 5, 10, 50 or 100 times the concentration (as determined, e.g., by weight/weight, chain number analysis or molarity) it is found in enoxaparin. In some embodiments, the subject population can be accompanied by a solvent, diluent, or carrier. In other embodiments, the subject population is substantially free of a solvent, diluent, or carrier. In some embodiments, the subject population can be accompanied by a medium, e.g., a buffer, matrix or other material used to effect separation and/or eluent, used in its purification. In other embodiments, the population is substantially free of such elements. In a preferred embodiment, the population is provided in an enclosure which is substantially free of contaminant carbohydrates.

The term "isolated population" as used herein refers to a population of saccharides containing chains having a specific reducing end structure that is substantially free of saccharides of at least one and preferably all other chains having other reducing end structures. Substantially free means that at least 70, 80, 90, 95, 99%, or substantially all, of a contaminating carbohydrate having other reducing end structures have been removed. In some embodiments the subject population can be accompanied by a solvent, diluent, or carrier. In some embodiments the subject population can be accompanied by a medium, e.g., a buffer, matrix and/or eluent, used in its purification. In other embodiments the isolated population does not contain a solvent, diluent, carrier or medium used in purification. In a preferred embodiment, the isolated population is provided in an enclosure which is free of contaminant saccharides having other reducing end structures. In sonic embodiments, in the case of a subject population which is present in UFH, the subject population is present in the isolated population at at least 2, 5, 10, 50 or 100 times the concentration (as determined, e.g., by weight/weight, chain number analysis or molarity) it is found in UFH. In some embodiments, in the case of a subject population which is present in enoxaparin, the subject population is present in the isolated population at at least 2, 5, 10, 50 or 100 times the concentration (as determined, e.g., by weight/weight, chain number analysis or molarity) it is found in enoxaparin.

The term "purified population" as used herein refers to a preparation containing a subject size class, that is at least 70, 80, 90, 95, 99% the subject size class or is substantially all subject size class. This determination can, by way of example, be based on weight/weight or chain number analysis. In sonic embodiments the subject size class can be accompanied by a solvent, diluent, or carrier. In some embodiments the subject size class can be accompanied by a medium, e.g., a buffer, matrix and/or eluent, used in its purification. In other embodiments the purified preparation does not contain a solvent, diluent, carrier or medium used in purification. In a preferred embodiment the purified preparation is provided in an enclosure which is substantially free of contaminant carbohydrates. In some embodiments, the case of a subject size class which is present in UFH, the subject size class is present in the purified preparation at at least 2, 5, 10, 50 or 100 times the concentration (as determined, e.g., by weight/weight, chain number analysis or molarity) it is found in UFH. In some embodiments, in the case of a subject size class which is present in enoxaparin, the subject size class is present in the purified preparation at at least 2, 5, 10, 50 or 100 times the concentration (as determined, e.g., by weight/weight, chain number analysis or molarity) it is found in enoxaparin.

In one aspect, the invention features, a method of making one or more batches of a polysaccharide preparation, wherein one or more glycoprofile values (e.g., one or more structural property, e.g., the presence, size distribution, or quantity of a 1,6 anhydro derivative, e.g., a 1,6 anhydro species described herein, referred to occasionally herein as a structural signature), of the batches varies less than a preselected range or generally has some preselected relationship with a reference standard. For example, it is present at a lower, higher, or equivalent level as a standard or is within (or outside) a range of values. Preferably, evaluation of the value, e.g., the presence of a 1,6 anhydro species, is made by a method described herein. In some embodiments, the method further includes classifying, selecting, accepting or discarding, releasing or withholding, processing into drug product, shipping, formulating, labeling, packaging, releasing into commerce, selling one or more batches having a structural property that varies less than the preselected range, e.g., a range described herein.

In another aspect, the invention features, multiple batches of a polysaccharide preparation, wherein one or more glycoprofile values for each batch varies less than a preselected range from a pre-selected desired glycoprofile, e.g., a range described herein for enoxaparin. In some embodiments, the method includes determining presence, amount or size distribution of a structural moiety of one or more batches of a product, and selecting a batch as a result of the determination. In some embodiments, the method can also include comparing the results of the determination to preselected values, e.g., a reference standard. In other embodiments, the method can further include adjusting the dose of the batch to be administered, e.g., based on the result of the determination of the structural signature. Preferably, evaluation of the value, e.g., the presence of a 1,6-anhydro species, is made by a method described herein.

In another aspect, the invention features, a method of determining a reference standard for a composition, e.g., a drug, by analyzing a sample, a sample including a composition including a mixed population of polysaccharides, such as glycosaminoglycans (GAGs), HLGAGs, UFH, or LMWHs, including but not limited to enoxaparin (Lovenox™ or Clexaner™); dalteparin (Fragmin™); certoparin (Sandoparin™); ardeparin (Normiflo™); nadroparin (Fraxiparin™); parnaparin (Fluxum™); reviparin (Clivarin™); tinzaparin (Innohep™ or Logiparin™), or Fondaparinux (Arixtra™), and determining if a structural moiety, e.g., a 1,6-anhydro species or mixture of 1,6 anhydro species is present, e.g., a species described herein including those provided in FIG. 1 and FIG. 2. Preferably, evaluation of the value, e.g., the presence, size distribution, or quantity of a structural moiety, e.g., a 1,6-anhydro species, is made by a method described herein.

In another aspect, the invention features, a method for determining bioequivalence. The method includes some or all of the following: providing or determining a value for the presence, amount or size distribution of a structural moiety, e.g., a 1,6 andydro structural moiety, in a first sample; providing or determining the bioavailability of the sample; providing a reference value, e.g., by providing or determining presence, amount or size distribution of a structural moiety, e.g., a 1,6 anhydro structural moiety, in a second sample, and comparing the amount or size distribution of the structural moiety, e.g., the 1,6 anhydro structural moiety, of the first sample and/or the reference value, e.g., a second sample. In some embodiments, the reference value can include one or more of the ranges described herein for enoxaparin. Preferably, evaluation of the structural moiety is made by a method described herein.

In some embodiments, the method further comprises monitoring for presence, tissue distribution, spatial distribution, temporal distribution or retention time, in a cell or a subject, e.g., an experimental animal. In some embodiments, the method includes determining the amount or size distribution of a structural moiety, e.g., a 1,6 anhydro structural moiety, of one or more batches of a product. In some embodiments, the method further includes selecting a batch as a result of the determination. In some embodiments, the method further includes comparing the results of the determination to preselected values, e.g., a reference standard.

In one aspect, the invention provides, a method of producing a LMWH preparation having or not having a pre-selected biological activity as a result of the presence, amount or size distribution of a structural moiety, e.g., a 1,6 anhydro structural moiety, e.g., one or more of the 1,6 anhydro structure of FIG. 1 or FIG. 2. Preferably, evaluation of the presence, amount or size distribution of a structural moiety, e.g., a 1,6-anhydro species is made by a method described herein. The method can include some or all of the following: providing one or more aliquots of heparin; optionally fractionating the heparin; modifying the aliquots of heparin under conditions designed to produce the activity; and optionally purifying the digested aliquots. In some embodiments, the desired biological activity is an effect on cellular activities such as cell growth or proliferation; cellular migration, adhesion, or activation; neovascularization; angiogenesis; coagulation; and inflammatory processes. In some embodiments, the desired biological activity is anti-IIa activity; anti-Xa activity; platelet factor 4 binding; FGF binding; or sensitivity to neutralization with protamine. In some embodiments, the desired biological activity is anti-IIa activity and anti-Xa activity. In some embodiments, the aliquots are modified by chemically or enzymatically digesting, the LMWH or UFH, e.g., by enzymatic digestion carried out using one or more heparin degrading enzymes, e.g., any of the heparin degrading enzymes described herein, and mixtures thereof. In some embodiments, the chemical digestion is carried out by a chemical chosen from the group consisting of oxidative depolymerization with $H_2O_2$ or $Cu+$ and $H_2O_2$, deaminative cleavage with isoamyl nitrite, or nitrous acid, β-eliminative cleavage with benzyl ester or by alkaline treatment. In some embodiments, the method also includes testing the LMWH preparation for the desired biological activity.

In another aspect, the invention provides a method for determining the safety or suitability of a heparin, e.g., a LMWH, for use in a particular indication. The method includes some or all, typically all, of the following: determining the presence, amount or size distribution of a structural moiety, e.g., a 1,6 anhydro structural moiety, in the heparin; providing a reference value or sample; determining if the heparin is acceptable, e.g., by comparing a value for the presence, amount or size distribution of a structural moiety, e.g., a 1,6 anhydro structural moiety, of the heparin with the reference value or with a value determined from the sample. For example, when the heparin is enoxaparin, one or more of the ranges described herein can be used as a reference value. When a preselected index of similarity is met, the heparin can be determined to be safe or suitable. In some embodiments, the reference sample is associated with one or more undesired effects. In some embodiments, the reference sample is associated with one or more desired effects. Preferably, evaluation of the presence, amount or size distribution of a structural moiety, e.g., a 1,6 anhydro species, in the heparin is made by a method described herein.

In another aspect, the invention provides, a method of making one or more batches of a LMWH preparation which has a batch-to-batch variation within a preselected range for a preselected value for a parameter (e.g., presence, amount or size distribution) related to one or more structural moiety, e.g., 1,6 anhydro saccharides. In some embodiments, the preselected range for to preselected value for a parameter (e.g., presence, amount or size distribution) related to one or more 1,6 anhydro saccharides can be one or more of the ranges described herein. The method can further include classifying, selecting, accepting or discarding, releasing or withholding, processing into a drug product, shipping, formulating, labeling, packaging, releasing into commerce, selling the preparation based, a batch based upon the presence of the parameter within a preselected range.

In one aspect, the invention features a method of, providing a report to a report receiving entity, evaluating a sample of heparin, e.g., LMWH, e.g., enoxaparin, for compliance with a reference standard, e.g., an FDA requirement, seeking indication from other party that an enoxaparin sample meets some predefined requirement, or submitting information about an enoxaparin sample to another party. Exemplary receiving entities or other parties include a government, e.g., the U.S. federal government, e.g., a government agency, e.g., the FDA.

The method includes one or more (and preferably all) of the following: making and/or testing a batch of the heparin in a first country, preferably the US;

sending at least an aliquot of the sample outside the first country, e.g., sending it outside the United States, to a second country;

preparing, or receiving, a report which includes data about the structure of the enoxaparin sample, e.g., data related to a 1,6 anhydro structure, e.g., data generated by one or more of the methods described herein;

providing said report to a report recipient entity.

In a preferred embodiment the report receiving entity can determine if a predetermined requirement or reference value is met by said data and optionally, a response from the report receiving entity is received, e.g., by a manufacturer, distributor or seller of the heparin. In a preferred embodiment, upon receipt of approval from said report recipient entity, heparin from said batch is selected, packaged, or placed into commerce.

In one aspect, the invention features a method of evaluating a sample of heparin, e.g., LMWH, e.g., enoxaparin, that includes receiving data with regard to the presence or level of a structural moiety, e.g., a 1,6 anhydro structural moiety, in a heparin sample, e.g., wherein the data was prepared by one or more methods described herein; providing a record which includes said data and optionally includes an identifier for a batch of heparin; submitting said record to a decision-maker, e.g., a government agency, e.g., the FDA; optionally, receiving a communication from said decision maker; optionally, deciding whether to release market the batch of heparin, e.g., Lovenox or enoxaparin, based on the communication from the decision maker. In one embodiment, the method further includes releasing the sample.

A "polysacharide" as used herein is a polymer composed of monosaccharides linked to one another. In many polysaccharides, the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide). Polysaccharides include but are not limited to heparin-like glycosaminoglycans, chondroitin sulfate, hyaluronic acid and derivatives or analogs thereof, chitin and derivatives and analogs thereof e.g., 6-O-sulfated carboxymethyl chitin, immunogenic polysaccharides isolated from phellinus linteus, PI-88 (a mixture of highly sulfated oligosaccharide derived from the sulfation of phosphomannam which is purified from the high molecular weight core produced by fermentation of the yeast *pichia holstii*) and its derivatives and analogs, polysaccharide antigens for vaccines, and calcium spirulan (Ca-SP, isolated from blue-green algae, spirulina platensis, K5 strain of *E. coli* or *Pasteurella multocida*) and derivatives and analogs thereof.

A polysaccharide according to the invention can be a mixed population of polysaccharides, e.g., a heparin, synthetic heparin, or LMWH preparation. As used herein, a "mixed population of polysaccharides" is a polydisperse mixture of polysaccharides. The term "polydisperse" or "polydispersity" refers to the weight average molecular weight of a composition (Mw) divided by the number average molecular weight (Mn). The polydispersity of unfractionated heparin and various LMWHs are known, as are methods for determining polydispersity. Compositions with polydispersity near 1 are more homogeneous, containing fewer polysaccharides of different chain lengths. As an example, a preparation of unfractionated heparin, which contains a wide variety of polysaccharides of differing lengths and compositions, has a polydispersity of about 1.5 to 2.0.

The details of one or more embodiments of the invention are set forth in the accompanying drawings and the description below. Other features, objects, and advantages of the invention will be apparent from the description and drawings, and from the claims.

DETAILED DESCRIPTION

The drawings are first briefly described.

Figure 4:
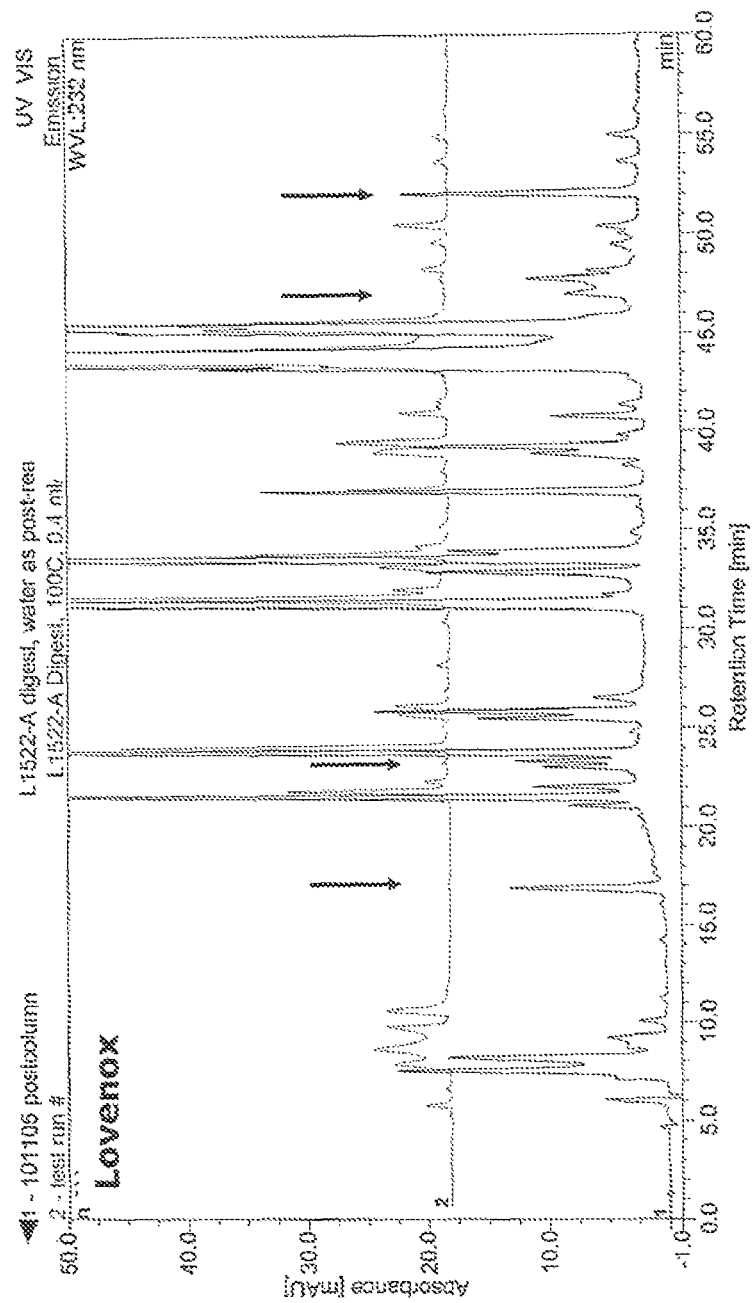

FIG. 4 shows the chromatographic separation representative for enoxaparin. Fluorescent absorption is shown on top and UV absorbance below. Arrows indicate 1,6 anhydro structures that have UV absorbance but are not labeled and hence have no fluorescence.

Figure 5:
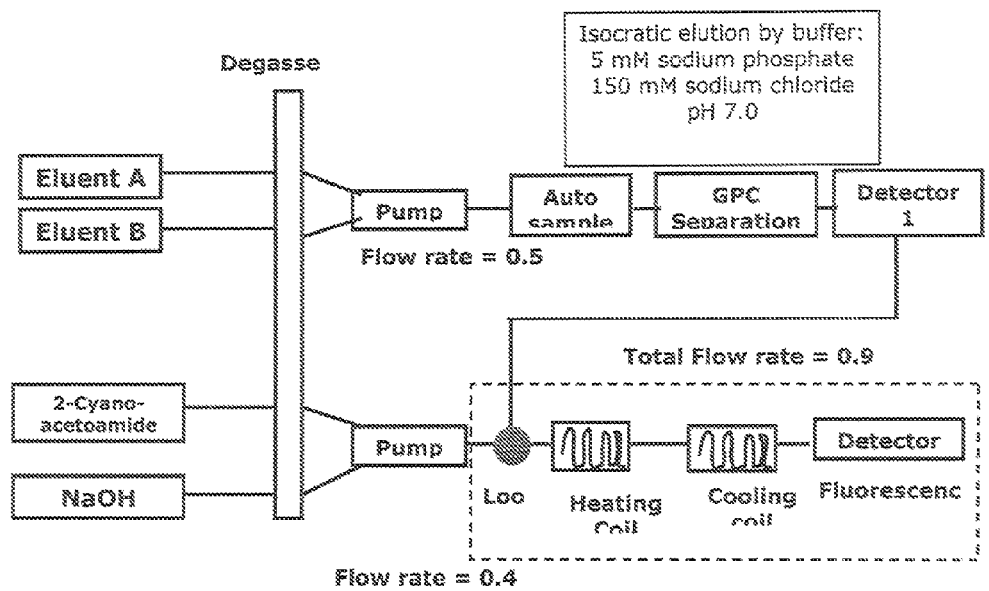

FIG. 5 depicts an HPLC system that can be used to analyze total UV and fluorescent labeled reducing structural moieties of a size fractioned sample.

Figure 6:
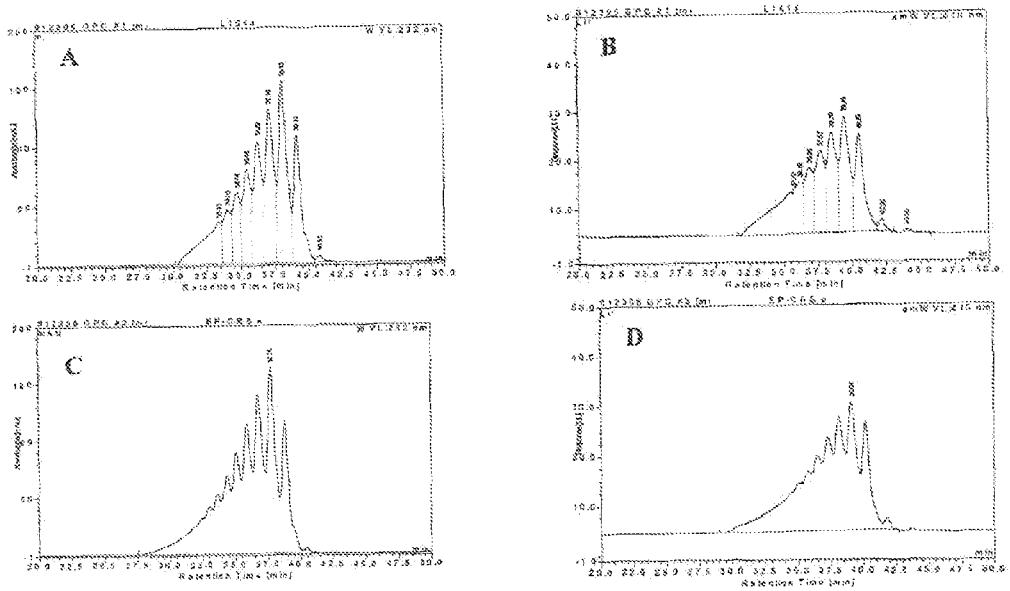

FIG. 6 shows the chromatographic separation representative for a batch of enoxaparin and an enoxaparin EP standard; (A) depicts the UV profile of enoxaparin; (B) depicts the Em410 profile or enoxaparin (C) depicts the UV profile of EP-CRS; (D) depicts the Em410 profile of EP-CRS.

Figure 7:
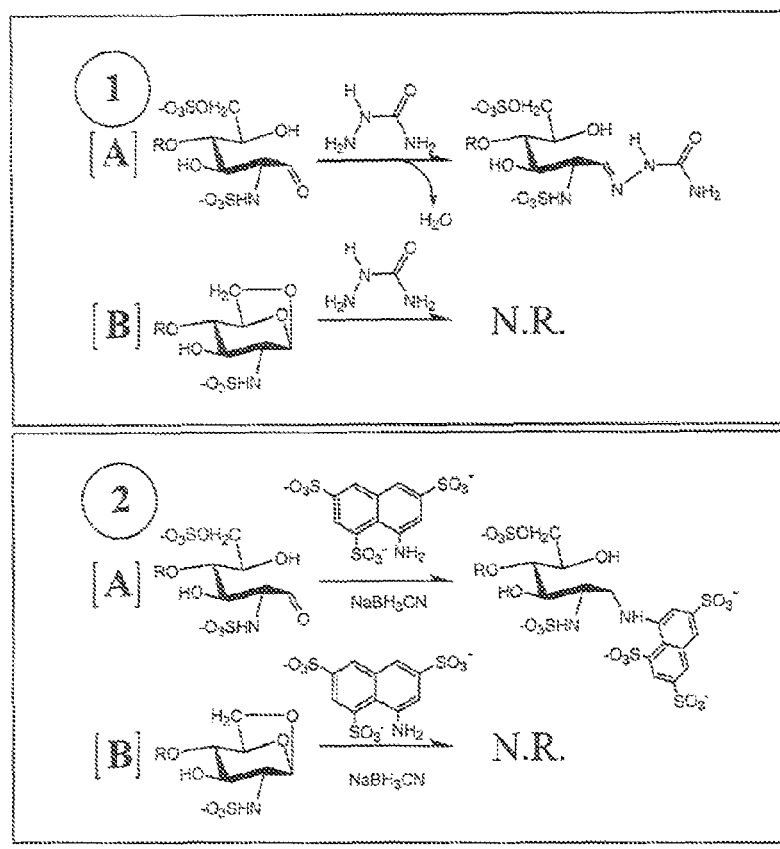

FIG. 7 shows different chemical reaction schemes that can be used to differentiate 1,6 anhydro species from species that contain an unmodified reducing end.

Figure 8:
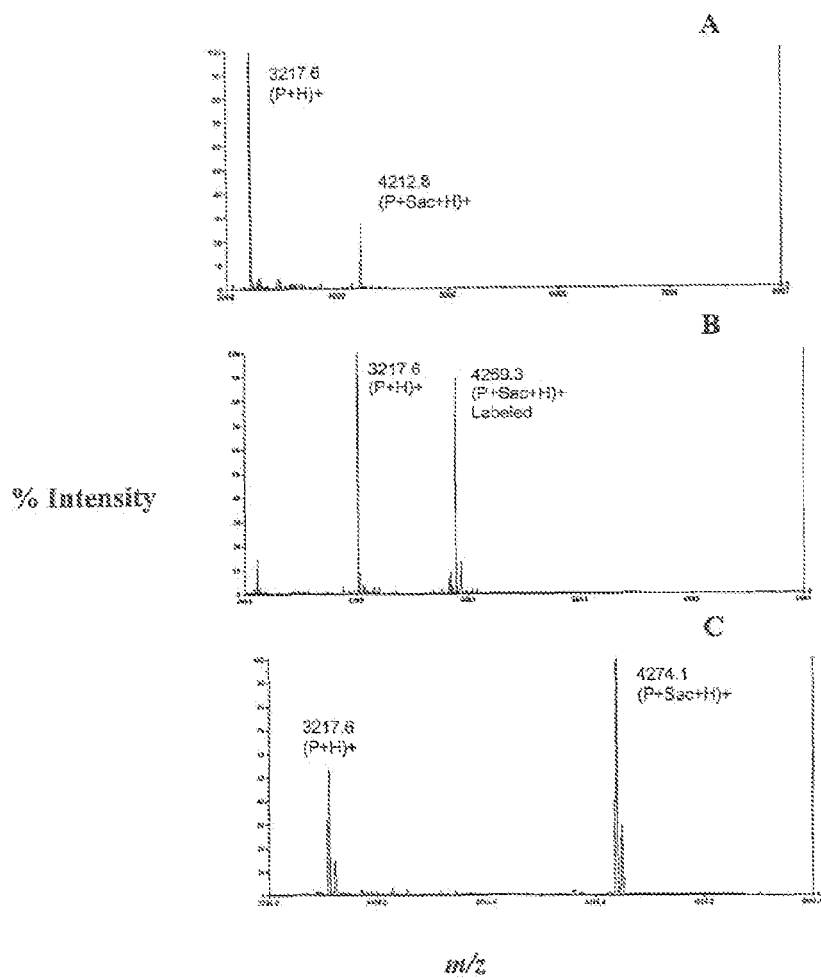

FIG. 8 shows matrix-assisted laser desorption ionization mass spectrometry data for a non-1,6 species (8A and 8B) and a 1,6 species (8C). Analysis of a non-1,6 species prior to derivatization by semi-carbazide yielded a mass of 995.2. (FIG. 8A). After reaction with semicarbazide, analysis of this same species yielded a mass shift to 1051.7, indicative of successful reaction with semicarbazide (FIG. 8B). Conversely, analysis of a 1,6 species after reaction, gave no mass shift (FIG. 8C, mass is 1056 before and after reaction).

Figure 9:
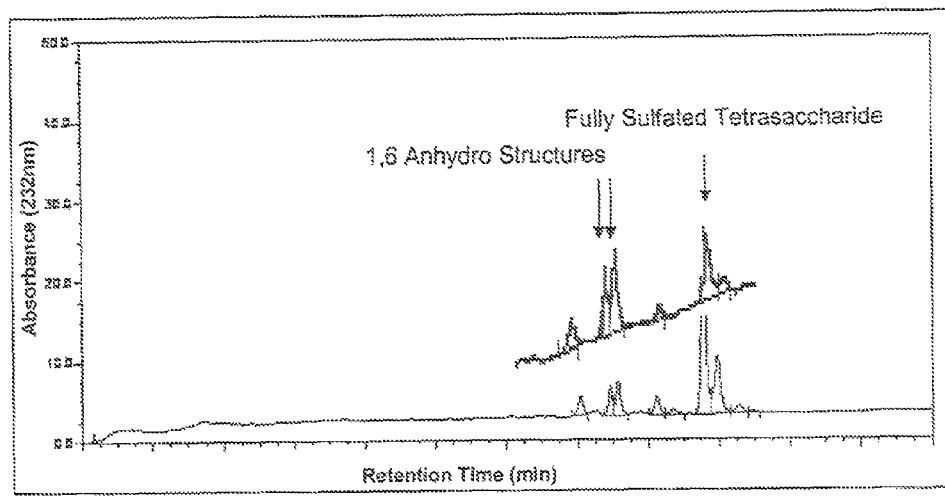

FIG. 9 shows enrichment of 1,6 structures in a tetrasaccharide pool of enoxaparin. Shown is the mixture before running over a hydrazide column (black) and after running over the hydrazide column (red, inset).

A variety of analytical techniques can be used to analyze polysaccharide mixtures or subsets of the mixtures that are representative of the polysaccharide as a whole, i.e. analysis of a size-defined saccharide pool to characterize the entire mixture, e.g., in LMWHs, such as enoxaparin and dalteprin, most of the chains are of even number (2,4,6,8 . . .). Each of these can be separated into a distinct pool, for example, the tetrasaccharide pool, the hexasaccharide pool, and so on. In particular, analytical techniques using reduce end labeling can be used to analyze mixtures of polysaccharides (such as a heparin or a LMWH) to provide a determination of the presence and/or amount of a particular structural motif, e.g., a 1,6 anhydro structural motif. In some instances, one or more polysaccharides in the mixture are chemically modified prior to analysis.

In some embodiments, the analytical methods can be used to analyze a LMWH such as enoxaparin or dalteparin. Dalteparin has been found to contain a unique 2,5-anhydromannitol moiety (structure V) while enoxaparin has been identified to have a unique 1,6 anhydro structure at the reducing end (IV) and a 4,5 double bond at the non-reducing end (I) as depicted below:

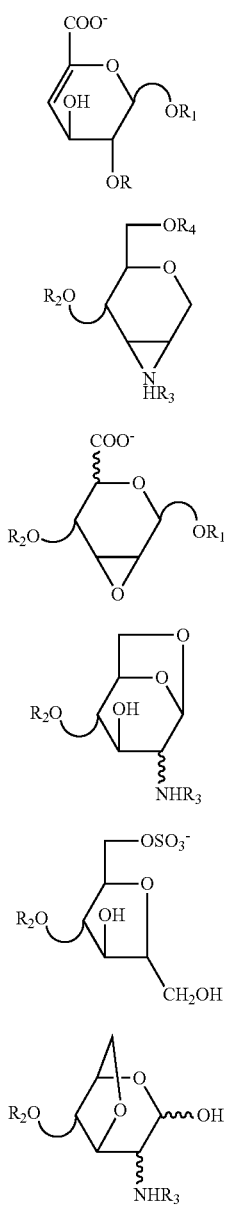

R=SO$_3$ or H; R$_1$: Glc—NH (SO$_3$H or COCH$_3$) (I/G 2 (SO$_3$ or H) Hex N (SO$_3$H or COCH$_3$) -3 (H or SO$_3$H), -6 (H or SO$_3$H))n, n=0 to 20; R$_2$: (I/G/ΔU 2 (SO$_3$ or H) Hex N (SO$_3$H or COCH$_3$) -3 (H or SO$_3$H), -6 (H or SO$_3$H))n I/G/ΔU -2 (H or SO$_3$H), wherein n =0 to 30; R$_3$: H or SO$_3$H or COCH$_3$; R$_4$: H or SO$_3$H. These structures are also referred to herein as the structure of "formula I", "formula II", "formula III", "formula IV", "formula V" and "formula VI". "I" is iduronic acid; "G" is glucuronic acid; "Glc" is glucose; "Hex" is a hexosamine.

All of the oligosaccharide structures may be present in various complex polysaccharides, especially ones containing one or more uronic acids and/or N-substituted hexosamines, for example heparins, dermatans, etc. That these posses biological activity has been shown. For example, structures of the formula II appear within the context of the AT-III binding site and thus impinge on the anticoagulant activity of the LMWH preparation. Similarly, non-reduced structures of formula V, containing an aldehyde instead of a primary alcohol, can react with serum proteins to extend the in vivo half-life of the molecule. Oligosaccharides of the formula V having the 2,5 anhydro structures have no negatively charged sulfonamino group at the reducing end of the molecule unlike other structures (I- IV, and VI). It has been reported in the literature that this structural property minimizes the cellular interactions and protects the larger size oligosaccharides from elimination. They remain in the circulation, contributing longer lasting anti-Xa activity by binding tissue factor pathway inhibitor (TFPI).

Also, oligosaccharides of the formula IV have been suggested to have anti-inflammatory properties and can thus be used for preventing or treating diseases associated with an inflammatory process involving the production of cytotoxic substances such as nitrogen monoxide (NO) whose inducible form is released in particular by neutrophils or macrophages when the latter migrate and are activated in a tissue. The activation, migration, adhesion and infiltration of neutrophils takes place in ischemic tissue regions following an occlusion or spasm of an artery vascularizing this tissue. These ischemias can arise either in the brain (cerebrovascular accident) or in the myocardium (myocardial infarction) or in the lower limbs (so-called peripheral ischemias). The oligosaccharides of formula IV can thus be used for the prevention and/or treatment of neurodegenerative diseases for which such inflammation plays a deleterious role which can lead to death, among which mention may be made of cerebral ischemias, cardiac ischemias (myocardial infarction), peripheral ischemias, traumas of the central nervous system, in particular, cranial, spinal and craniospinal traumas, multiple sclerosis, neuropathic pain and peripheral neuropathies, motor neuron diseases including amyotrophic lateral sclerosis, neuro-AIDS, Alzheimer's disease, Parkinson's disease and Huntington's chorea and certain forms of osteoarthritis, in particular of articular localization.

Applicants have identified a variety of methods for analyzing a polysaccharide mixture such as a heparin or a LMWH (e.g., enoxaparin) to identify the presence, and in some instances, quantify the amount or size distribution of a structural moiety for example a structure 1,6 anhydro (e.g., the structure of formula IV), in a polysaccharide mixture. Some of these methods do not require or do not include the isolation of the molecule being analyzed.

Reducing End Labeling

Low molecular weight heparin mixtures such as enoxaparin are size disperse and inhomogeneous in structure and sequences. In the case of enoxaparin, the non-reducing terminal contains mostly Δ4,5-bonds (ΔU) due, e.g., to the alkaline elimination of glycosidic bonds in unfractionated heparin. The Δ4,5-bond possesses UV absorbance with a λmax of 232 nm. Quantification of the number of Δ4,5-bonds using a UV detector at 232 nm can be used to estimate the number of chains. In contrast, the structure of reducing end of enoxaparin is inhomogeneous. Generally speaking, the reducing end of enoxaparin is comprised of three major entities: (1) semiacetals (~80%), (2) aldehydes (0.5%) or (3) acetals (15-25%). The former two functional groups (semiacetal and aldehyde, also referred to as "free" reducing ends) are much more reactive. Semiacetal and aldehyde are examples of "open ring confirmation structural moieties" as used herein, while acetals such as 1,6 anhydro structural moieties are examples of "close ring confirmation structural moieties".

The methods described herein can be performed, e.g., on a digested polysaccharide sample (e.g., a sample digested with one or more heparin degrading enzymes to obtain, e.g., a sample of one or more of di-, tri-, tetra- or pentasaccharides), a size fractionated pool obtained from a polysaccharide sample (e.g., one or more size classes that exist in the polysaccharide sample, e.g., one or more of the tetra-, hexa-, octa-, deca-, dodeca-, etc., saccharide fraction), or on an undigested, unfractionated polysaccharide sample.

Labeling of free reducing ends in complex polysaccharides can be achieved using a detectable moiety, e.g., a reporter group which will not label modified reducing ends. The reducing ends can be labeled with a molecule containing a free primary amine functionality in the presence of a reducing agent. In this case, modified reducing ends will not be labeled. For example, addition of excess biotin hydrazide results in biotinylation of chains containing free reducing ends.

Biotinylated chains can be captured on a strepTavidin surface or bead. The material that is not bound is washed off and the $U_{232}$ is determined. For example, for enoxaparins, it has been determined the concentration of saccharide structures, e.g. 1,6-anhydro structures, can be determined based on $UV_{232}$ readings. The ratio of $UV_{232}$ reading of unbound material to $UV_{232}$ reading of starting material will yield the percentage of 1,6-anhydro or 2,5-anhydro chains in the mixture. Reductive amination using a primary amine and an excess of reducing agent, such as sodium borohydride, was used to effect the labeling of the reducing end. Or, an aminooxyacetyl peptide that is biotinylated can be used. The aminooxyacetyl reaction with an aldehyde or ketone (such as with the reducing end of a saccharide) is known to be a very specific reaction that can occur under a number of conditions, including physiological ionic strength and pH. Instead of biotin hydrazide, a peptide with an aminooxy moiety at the N terminus and a biotin tag at the C-terminus can be used to react selectively with the ends of saccharides that do not contain an anhydro structure at the reducing end.

The amount of Lovenox™ (enoxaparin) which was used for a biotinylation reaction was determined by $UV^{232}$ readings using the Lovenox™ standard curve. Biotinylation of reducing end chains of Lovenox™ (1 mg/mL in water) which are not modified were performed by addition of 50 mM biotin-LC-hydrazide (Pierce) in DMSO to give a final concentration of 5 mM. The solution was securely capped, mixed end-over-end for 24 hrs at room temperature. The reaction mixture was applied to 5 mL DEAE-Sephacel column equilibrated with 10 mM Na phosphate/50 mM NaCl pH=7.0. After washing with the same solution to remove unreacted biotin reagent, the bound oligosaccharides (which contain bath biotinylated and non-biotinylated chains) were eluted with 10 mM Na phosphate/1.5 M NaCl pH=7.0 lyophilized, reconstituted in water and desalted by passing through a P-2 column and elated with water.

Biotinylated chains were captured on Magnetic Porous Glass (MPG) Streptavidin beads (CPG Biotech). After equilibrating the beads with binding buffer Phosphate-buffered saline pH 7.4, the oligosaccharide solution was added, mixed end-over-end for 1 hr at room temperature, and magnetically separated. The material that was not bound was washed of with washing buffer (PBS pH=7.4) and $UV_{232}$ was determined. In this example 1,6 anhydro structures were quantified without any chromatographic separation.

The 1,6-anhydro percentage from an enoxaparin sample was determined by the ratio of $UV_{232}$ reading of unbound material to $UV_{232}$ reading of starting material as shown in Table 1.

|  | UV232 |
|---|---|
| Before Selection | 1.0 |
| After Selection | 0.22 |

Thus, in this experiment, 22% of the chains were found to contain a reducing end with a 1,6 structure.

Another method of analyzing non-1,6 anhydro reducing ends utilizes a hydrazide column. UltraLink Hydrazide gel is an affinity support for immobilizing samples containing reactive aldehyde groups. The aldehydes can react hydrazide groups on the UltraLink Hydrazide Gel to form stable hydrazone bonds. The coupling conditions are flexible with regard to time and temperature. This method isolates LMWH ingredients that contain 1,6-anhydro ring structures at the reducing end from the LMWH mixtures. By shifting the equilibrium of carbohydrate to the linear form, the non 1,6-anhydro constituents are covalently immobilized to the hydrazide gel solid phase and the 1,6-containing linkages flow through and can be filtered out from the gel matrix.

A tetrasaccharide pool of Lovenox was chosen as a model sample to demonstrate the proof of this principle. For Lovenox, prior to fractionation treatment to obtain the tetrasaccharide pool, approximately 10 to 25% of the mix is 1,6 anhydro. For the fractionated sample, this increases to greater than 50% of the mixture.

An UltraLink Hydrazide gel, 10 ml resin, 20 mL slurry (Pierce Biotechnology, Inc. Catalog # 53149) supplied as a 50% slurry in 0.02% sodium azide was used. A 0.5 hydrazide gel slurry was applied to 1 ml empty spin column (Novagen or Biorad), spin 0.5 min at 0.8 k rpm. Buffer exchange was performed three times with the addition of 0.5 mL coupling buffer (50 mM Sodium acetate and 30% ethanol, pH 5.5) to the gel (centrifuge column 0.5 min at 0.8 k rpm and discard the buffer). A 100 µl aliquot of coupling buffer was added to the gel and transfer the slurry gel to 1.5 mL Eppendorf tube. A 100 µl aliquot of the tetrasaccharide pool of enoxaparin was added (5 mg/ml, 500 µg sugar totally) to the slurry gel, mixed and incubated at 60° C. for 2 hours. The coupling gel mixture was cooled and transferred the empty spin column. The filled column was centrifuged for 1 min at 0.8 k rpm, and the filtrate was collected and lyophilize to obtain white powder. The recovered sample was analyzed by SAX-HPLC, CE or UV absorbance to obtain the percentage of 1,6-anhydro constituents. Shown in FIG. 8 is separation and analysis using a Dionex ICS-3000 system, Carbopac PA1 4×250 mm column with a linear gradient of mobile phase A: 0.2 M NaCl, pH 3.5 and mobile phase B: 2 M NaCl, pH 3.5

In this case the tetra-pool of enoxaparin was chosen as a model sample to demonstrate the proof of concept for the 1,6-anhydro component isolation, but this can be extended to the entire mixture. The percentage of 1,6-anhydro contents can be measured using the following equations:

$$1,6\% = C' \times \frac{W_{flow-through}}{W_T} \times 100\%$$

$$1,6\% = C'' \times \frac{A_{flow-through}}{A_T} \times 100\%$$

In another example, the entire enoxaparin sample was analyzed. In this case, 800 µl of hydrazide gel slurry was rinsed with 800 µL of "Coupling buffer 2" (30% ethanol, pH 3.5 adjusted with acetic acid) three times. Then, 24 µl of 100 mg/ml enoxaparin solution was diluted with 576 μL of "Coupling buffer 1" (50 mM Sodium acetate and 30% ethanol, pH 5.5) to a final solution of 4 mg/mL enoxaparin. This sample was divided into three samples for treatment with hydrazide gel under various coupling conditions and one control (incubation in coupling buffer in the absence of hydrazide gel). The three samples were individually, directly applied to hydrazide gel.

For example, in one reaction, 400 μg of the enoxaparin sample solution was mixed with the hydrazide gel in a 1.5 ml Eppendorf tube and incubated at 37° C. for 24 hours, under agitation. This coupling mixture was then transferred to an empty spin column and centrifuged for 2 min at 1,000 rpm. The flow-through solution was collected and measured at a UV absorbance of 232 nm. Meanwhile the UV absorbance (232 nm) of the controlled sample was also recorded. By using the above formula, the percentage of 1,6-anhydro contents was determined to be ~16-20%.

In some embodiments, the molecule includes a moiety which promotes detection, e.g., a fluorescent reporter or radioactivity. In one embodiment, if the nucleophile is a fluorescent labeling reagent, then the products of derivatization are fluorescent. For instance, 2-cyanoacetamide is widely used as derivative reagent, and the derivatized product is fluorescent ($Ex_{max}$346 nm, $Em_{max}$=410 nm). However, acetal functional groups (such as the 1,6-anhydro ring structure) are inert and do not further derivatize under reactive conditions that label semiacetals or aldehydes. Thus, 1,6-anydro or 2,5-anhydro structures, which do not contain a free reducing end, will not be labeled. By quantifying the amount of fluorescence associated with sugars followed by normalizing the UV reading of the complex polysaccharide (for example, $UV_{232}$, indicative of the number of non-reducing ends, i.e. ΔU), the anhydro content in the whole mixture can be determined.

Figure 1:
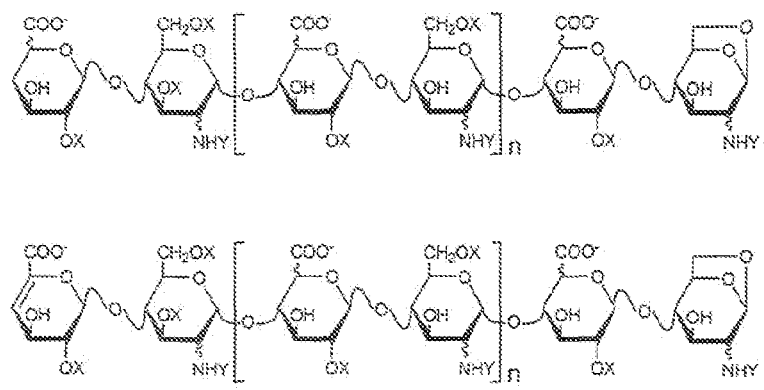
FIG. 1 shows 1,6 anhydro structures.
Figure 2:
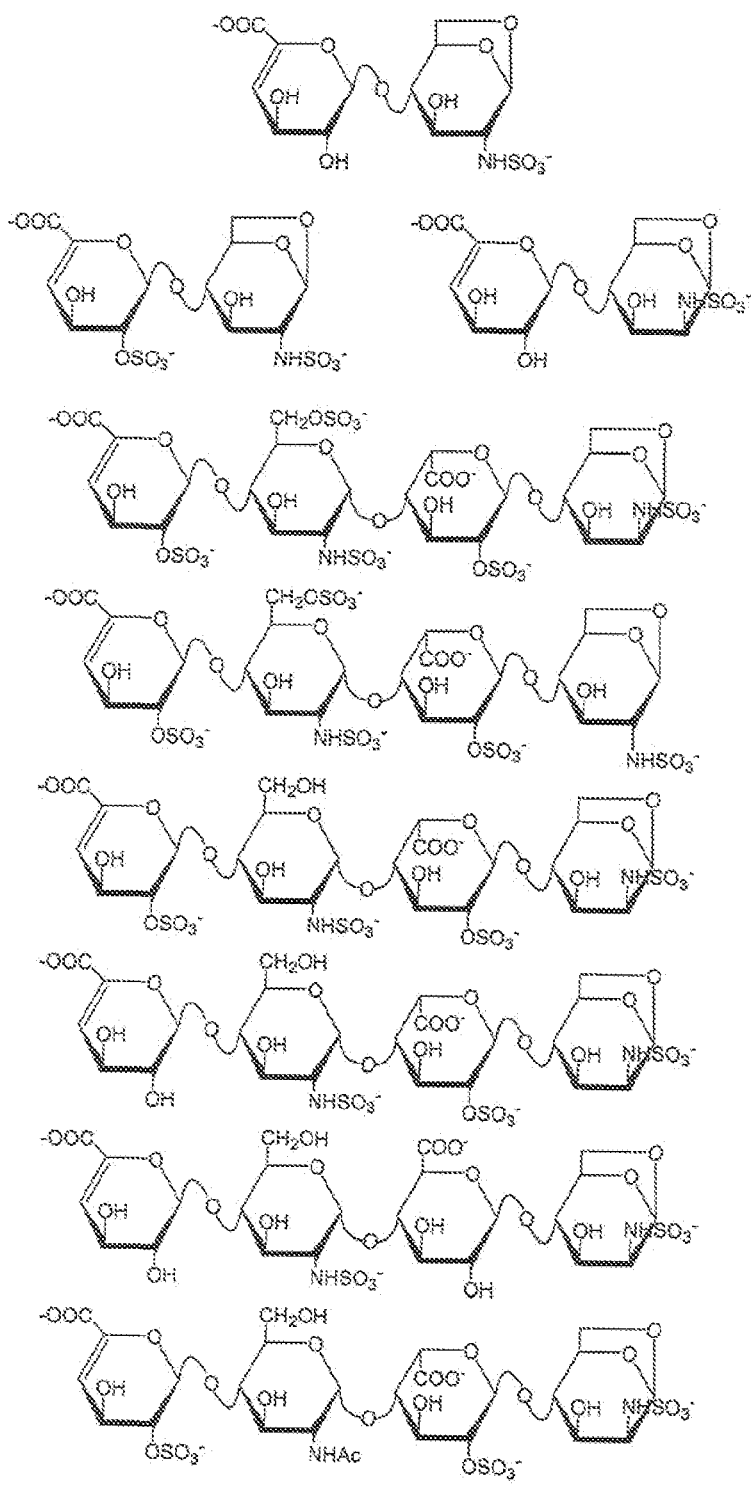
FIG. 2 shows 1,6 anhydro structures in a digested enoxaparin sample.
Figure 3:
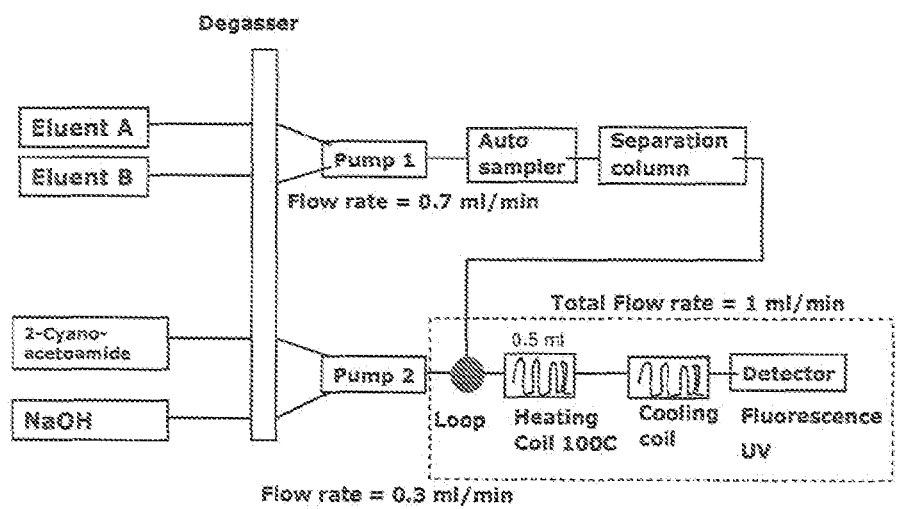
FIG. 3 depicts an HPLC system that can be used to analyze total UV and fluorescent labeled reducing structural moieties of a digested enoxaparin sample.

An example of a Dionex HPLC system used to evaluate such methods is shown in FIG. 2. After separation, the material flowed into a reaction coil, where it reacted with 2-cyanoacetamide under basic conditions. Results from such a readout are shown in FIG. 3.

As discussed herein, a sample, for example a LMWH such as enoxaparin, can be size fractionated before analysis. The method can quantify the 1,6-anhydro content in enoxaparin using, e.g., a GPC-HPLC method.

For example, enoxaparin was size separated by analytical GPC, monitored by UV absorbance at 232 cm. This UV response was proportional to the total molar amount of enoxaparin loaded into the column. Then, the separated size pools were further derivatized by 2-cyanoacetomide under basic condition under high resolution mode (Post column derivatization). This derivatization was stoichiometric and the product was fluorescent. The fluorescence readout was proportional to the molar amount of semiaectal and aldehydes (i.e. non-1,6-anhydro ring structures were all fluorescently derivatized, but the 1,6-anhydro were not and were undetectable by fluorescence). As a result, the subtraction of the fluorescence signal from the total number of chains detected by UV absorbance was used to determine the actual amount of 1,6-anhydro structure in the intake mixture. Two standards were used as controls: a positive control (100% derivativatizable, i.e. tinzaparin) and a negative control (0% derivativatizable, hydroxide modified BLH). A formula was derived as below is used to calculate the molar percentage of 1,6-anhydro content of an unknown enoxaparin sample.

$$\text{molar}\% = \left(1 - \frac{F_S}{A_S} \times \frac{A_C}{F_C}\right) \times 100$$

Where, $F_S$ is the total emission readout at 410 nm of sample, $A_S$ is the total absorbance readout at 232 nm of sample, $F_C$ is the total emission readout at 410 nm of the control sample, in this case tinzaparin, and $A_C$ is the total absorbance readout at 232 nm of the same control.

Briefly, the sample (control or unknown) was dissolved in running buffer (5 mM sodium phosphate, 150 mM sodium chloride) at a concentration of 10 mg/mL. 30-50 μl aliquot of sample solution was injected into a GPC column (two SEC columns G3000SW and G2000SW connected in series) and eluted under isocratic conditions. The elated fractions were first monitored by UV absorbance at 232 nm, then derivatized by 2-cyanoacetoamide under basic conditions (passing through a post column reaction heating and cooling coil). The post column derivatization was monitored using an emission wavelength at 410 nm and an excitation wavelength of 346 nm.

An example of a system used to evaluate such methods is shown in FIG. 6. After separation, the material flows into a reaction coil, where it reacts with 2-cyanoacetamide under basic conditions. Results from such a readout are shown in FIG. 7. The method described above was used to analyze a positive controlled sample (Tinzaparin), a lot of enoxaparin and EP-CRS (Enoxaparin EP standard). FIG. 7 and quantitative results for the lot of enoxaparin and EPCRS. A=UV profile of the lot of enoxaparin; B=$Em_{410}$ profile of the lot of enoxaparin; C=UV profile of EPCRS; D=$Em_{410}$ profile of EPCRS are shown. Quantitative data and an estimate of 1,6 is presented in the table below.

|  | A_232 | F_410 | 1,6-anhydro % |
| --- | --- | --- | --- |
| tinzaparin | 290.32 | 79.69 | 0 |
| enoxaparin | 526.37 | 98.28 | 27 |
| EP-CRS | 587.02 | 112.79 | 28 |

The size fractionated sample can be representative of 1,6 anhydro content of the sample as a whole. Radioactivity can also be used.

Alternatively, the detection can be another method, such as mass spectrometry. in this case, a molecule like semicarbazide can be used to selectively modify the reducing end of non-1,6 species, 1,6 species are not affected by semicarbazide (FIG. 6 and FIG. 8C). Derivatizations can be carried out, for instance by reacting an oligosaccharide solution (or set of oligosaccharides) with an excess of semicarbazide (50-100 molar excess) in 60 mM Tris/acetic acid (pH 7.0, prepared fresh daily) for 16 h at 30° C. Then, mass spectrometry can be employed using known methods. Analysis can also occur by CE and/or HPLC.

Analysis of a Size Fractionated Mixture of Polysaccharide

As an alternative to analyzing complex polysaccharides as a whole, the sample, e.g., heparin, can be size separated into uniform fractions. Size fractionations can be effected by a variety of methods e.g., size exclusion chromatography. E.g., a sample is loaded onto a column with Superdex 30 Prep Grade resin. The column is equilibrated with 5 mM $Na_2HPO_4$, 150 mM NaCl pH 7.2.

The size-fractioned material can be analyzed by any of the methods outlined above. Size separation of LMWHs into length-homogenous pools was accomplished using preparative FPLC, for example for a 1L Superdex 30 column. 50-500 mg of LMWH material was applied to the column at a concentration of 100 mg/mL in water and elated at 1.7 mL/min with a running buffer of 0.15 M NaCl with 5 mM $Na_2PO_4$ pH 7.0. The site defined saccharides were collected by a fraction collector, desalted and lyophilized to dryness. Size fractionated enoxaparin size defined saccharide mixtures were desalted by passing through Sephadex 0-10 (14×5 cm) column eluted with water at a 50 cm/hr.

Analysis of a Digested Mixture of Polysaccharides

The polysaccharide mixture can be digested, e.g., chemically and/or enzymatically digested, e.g., incompletely or preferably, completely digested, prior to analysis or processing. The enzymatic digestion can be carried out with one or more heparin degrading enzymes, e.g., one or more heparinase, heparin lyase, heparin sulfate glycoaminoglycan (HS-GAG) lyase, a lyase described as a glycoaminoglycan (GAG) lyase that can also degrade heparin, and/or any polypeptide described as a hydrolase, sulfatase/sulfohyrdolase, or glycosyl hydrolase/glycosidase. For example, the polysaccharide mixture can be digested with one or more of: an unsaturated glucuronyl hydrolase (e.g., *F. heparinum* Δ4,5 glycuronidase, *B. thetaiotaomicron* Δ4,5 glycaronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase, *B. thetaiotaomicron* 6-O-sulfatase, a mucin desulfating enzyme, mammalian N-acetylglucosamine-6-sulfatase, mammalian iduronic acid-2-sulfatase); a N-sulfamidase (e.g., *F. heparinum* N-sulfamidase, mammalian heparan-N-sulfatase); an arylsulfatase; a hexosaminidase; a glycosyl hydrolase (e.g., endo- N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV); an endoglucoronidase (e.g., mammalian heparanase); a heparin/heparan sulfate lyase (e.g. *Bacteroides thetaiotaomicron* HSGAG lyase I, *Bacteroides thetaiotaomicron* HSGAG lyase II, *Bacteroides thetaiotaomicron* HSGAG lyase III, *Bacteroides thetaiotaomicron* GAG lyase IV); and functional fragments and variants thereof. It can also include a polypeptide described as above (e.g.. GAG lyase, glycosyl hydrolase, sulfatase, sulfamidase, glucuronidase hexosaminidase, etc.) derived from microorganisms other than *Flavobacterium heparinum* (a.k.a. *Pedobacter heparinus*) or *Bacteroides thetaiotaomicron*. For example, *Haloarcula marismortui, Agrobacterium tumefaciens, Streptococcus pneumoniae, Streptococcus pneumoniae, Streptococcus pyogenes, Streptococcus agalactiae, Streptococcus intermedius, Streptococcus suis, Enterococcus faecalis, Rhodopseudomonas palustris, Nitrobacter winogradskyi, Nitrobacter hamburgensis, Bradyrhizobium japonicum, Rhizobium meloliti, Mesorhizobium loti, Spinghobacterium* sp. *Brucella abortus biovar, Brucella melitensis, Solibacter usitatus, Acidobacterium capsulatum, Microbulbifer degradans, Pseudomonas aeruginosa, Burkholderia pseudomonascepacia, Geobacter metallireducens, Prevotella* sp. *Serrata marcescens, Cornybacterium* sp., *Anaeromyxobacter dehalogenans, Rhodopirellula baltica, Pirellula marina,* and/or *Gemmata obscuriglobus*.

In one embodiment, the polysaccharide mixture is digested with *Flavobacterium heparinum* heparinase I, heparinase II and heparinase III. In one embodiment, the polysaccharide mixture is digested with *Bacteroides thetaiotaomicron* HSGAG lyase I, HSGAG lyase II, HSGAG lyase III and/or GAG lyase IV. In another embodiment, various combinations of heparinase(s) and HSGAG lyase(s) can be used in the digestion.

Any of the enzymes described herein can be replaced with an enzyme with functionally equivalent enzymatic activity.

The polysaccharide mixture can be digested using chemical digestion with a chemical agent, e.g., oxidative depolymerization, e.g., with $H_2O_2$ or Cu+ and $H_2O_2$, deaminative cleavage, e.g., with isoamyl nitrite or nitrous acid, β-eliminative cleavage, e.g., with benzyl ester, and/or by alkaline treatment.

The references, patents and patent applications cited herein are incorporated by reference. Modifications and variations of these methods and products thereof will be obvious to those skilled in the art from the foregoing detailed description and are intended to be encompassed within the scope of the appended claims.

What is claimed is:

1. A method of analyzing an enoxaparin sample, comprising:
providing an enoxaparin sample comprising a plurality of polysaccharide molecules;
detecting a Δ4,5 double bond associated with a non-reducing end of at least a portion of the polysaccharide molecules in the enoxaparin sample by UV absorbance, to determine the total number of chains in the sample;
detecting at least a portion of the polysaccharide molecules in the enoxaparin sample having a reducing end that has been reacted with a reactive moiety; and comparing the total number of chains in the sample to the number of chains labeled with the reactive moiety to quantify the amount of a 1,6 anhydro structural moiety in the sample,
wherein the enoxaparin sample is not further digested or depolymerized during the above process,
thereby analyzing the enoxaparin sample.

2. The method of claim 1, further comprising reacting a reducing end portion of at least a portion of the polysaccharide molecules in the enoxaparin sample with a reactive moiety.

3. The method of claim 1, wherein either the reducing end of a saccharide moiety or a 1,6 anhydro structural moiety in the enoxaparin sample is specifically reacted with the reactive moiety.

4. The method of claim 3, wherein either the reducing end of the saccharide moiety or the 1,6 anhydro structural moiety is quantified.

5. The method of claim 4, wherein at least a portion of the saccharides react with a label at the reducing end of the saccharide moiety.

6. The method of claim 4, wherein the enoxaparin sample is quantified by determining the amount of reacted saccharide.

7. The method of claim 1, wherein the reactive moiety is a fluorescent label.

8. The method of claim 1, wherein the reactive moiety does not react with 1,6 anhydro structural moieties.

9. The method of claim 1, wherein the reactive moiety reacts with polysaccharide molecules having a free reducing end.

10. The method of claim 9, wherein the reactive moiety reacts with semiacetals and aldehydes.

11. The method of claim 9, wherein the reactive moiety is cyanoacetamide.

12. The method of claim 1, wherein the reactive moiety is a biotin derivative.

13. The method of claim 12, wherein the biotin derivative is biotin hydrazide.

14. The method of claim 9, wherein the reactive moiety comprises a peptide comprising an aminoxy moiety at the C terminus.

15. The method of claim 14, wherein the peptide further comprises a biotin moiety.

16. The method of claim 1, wherein the enoxaparin sample is size fractionated.

17. The method of claim 16, wherein the size fractionated enoxaparin sample comprises a fraction selected from the group consisting of tetrasaccharides, hexasaccharides, octasaccharides, decasaccharides and dodecasaccharides.

18. The method of claim 4, wherein the amount or the size distribution of the 1,6 anhydro structural moiety is determined.

19. The method of claim 4, wherein the quantity of the reducing end of the saccharide moiety or the 1,6 structural moiety is quantified as a percent of total chains in the sample.

20. A method of analyzing a manufacturing process, the method comprising;
manufacturing an enoxaparin sample;
analyzing the enoxaparin sample using the method of claim 1 to identify and quantify at least a 1,6 anhydro moiety of the enoxaparin sample thereby allowing quantitative analysis, of the 1,6 anhydro moiety in the enoxaparin sample.

21. A method of comparing two enoxaparin samples to monitor or control batch-to-batch variation, the method comprising:
providing information regarding the quantity of a 1,6 anhydro moiety from a first enoxaparin sample obtained by the method of claim 1,
providing information regarding the quantity of a 1,6 anhydro moiety from a second enoxaparin sample obtained by the method of claim 1, and
comparing the quantity of the 1,6 anhydro moiety of the first enoxaparin sample with the quantity of the 1,6 anhydro moiety of the second enoxaparin sample.

* * * * *